(12) United States Patent
Chappel et al.

(10) Patent No.: US 11,020,572 B2
(45) Date of Patent: Jun. 1, 2021

(54) SYSTEM AND METHOD FOR CLEANING A FILTER

(71) Applicant: Debiotech S.A., Lausanne (CH)

(72) Inventors: Eric Chappel, Versonnex (FR); Dimitry Dumont-Fillon, Lausanne (CH)

(73) Assignee: Debiotech S.A., Lausanne (CH)

( * ) Notice: Subject to any disclaimer, the term of this patent is extended or adjusted under 35 U.S.C. 154(b) by 613 days.

(21) Appl. No.: 15/741,539

(22) PCT Filed: Jul. 8, 2016

(86) PCT No.: PCT/IB2016/054117
§ 371 (c)(1),
(2) Date: Jan. 3, 2018

(87) PCT Pub. No.: WO2017/006293
PCT Pub. Date: Jan. 12, 2017

(65) Prior Publication Data
US 2018/0193617 A1    Jul. 12, 2018

(30) Foreign Application Priority Data

Jul. 8, 2015   (EP) .................................... 15175963

(51) Int. Cl.
*A61M 27/00*   (2006.01)
*A61M 5/142*   (2006.01)
(Continued)

(52) U.S. Cl.
CPC ........ *A61M 27/006* (2013.01); *A61M 5/1428* (2013.01); *A61M 5/14212* (2013.01);
(Continued)

(58) Field of Classification Search
CPC .......... A61M 5/14212; A61M 5/14244; A61M 5/14276; A61M 5/1428; A61M 27/006;
(Continued)

(56) References Cited

U.S. PATENT DOCUMENTS

| 3,951,147 A | 4/1976 | Tucker et al. |
| 4,741,730 A * | 5/1988 | Dormandy, Jr. .... A61M 27/006 604/128 |

(Continued)

FOREIGN PATENT DOCUMENTS

| AP | 367 A | 1/1995 |
| EP | 2153855 A1 | 2/2010 |

(Continued)

OTHER PUBLICATIONS

International Search Report for PCT/IB2016/054117, dated Nov. 9, 2016.
(Continued)

*Primary Examiner* — Benjamin J Klein
(74) *Attorney, Agent, or Firm* — Andre Roland S.A.; Nikolaus Schibli

(57) ABSTRACT

The device presented is designed to cause, in a mode of operation referred to as "normal" mode, a fluid to flow along this fluid path successively through the first cavity, the filter, the second cavity then the flow restrictor. The device is also designed to cause, in a mode of operation referred to as "purge" mode, a fluid to flow along this same fluid path through the filter but in the opposite direction to the normal flow of the fluid (in the normal mode of operation). Thanks to the "purge" mode, the fluid will detach impurities that have become trapped on the filter in order to clean same.

19 Claims, 5 Drawing Sheets

Figure 1A:
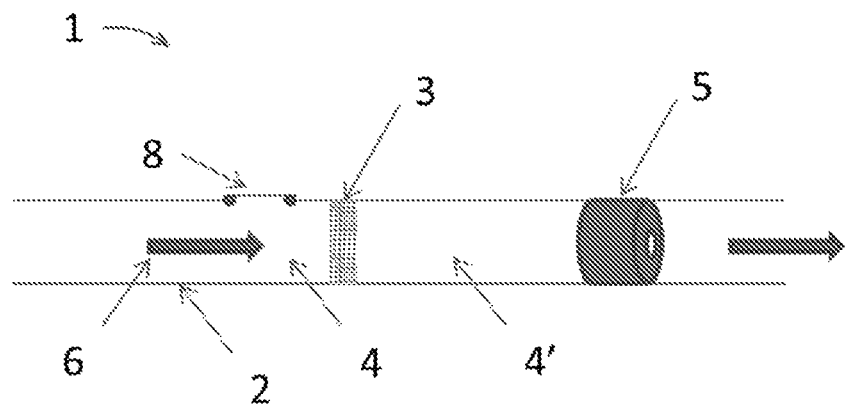

(51) Int. Cl.
*A61M 39/02* (2006.01)
*A61M 25/00* (2006.01)

(52) U.S. Cl.
CPC .... *A61M 5/14244* (2013.01); *A61M 5/14276* (2013.01); *A61M 39/0208* (2013.01); *A61M 2025/0019* (2013.01); *A61M 2039/0241* (2013.01); *A61M 2205/7554* (2013.01); *A61M 2209/10* (2013.01)

(58) Field of Classification Search
CPC ...... A61M 39/0208; A61M 2025/0019; A61M 2039/0241
See application file for complete search history.

(56) References Cited

U.S. PATENT DOCUMENTS

| | | | |
|---|---|---|---|
| 5,314,624 | A | 5/1994 | Kawakura et al. |
| 8,273,253 | B2 | 9/2012 | Curran |
| 8,539,981 | B2 | 9/2013 | Chappel |
| 8,790,318 | B2 | 7/2014 | Chappel |
| 8,869,826 | B2 | 10/2014 | Chappel et al. |
| 9,971,358 | B2 | 5/2018 | Chappel |
| 2004/0260229 | A1* | 12/2004 | Meir ...................... A61B 5/031 604/9 |
| 2010/0234793 | A1 | 9/2010 | Dacey, Jr. et al. |
| 2010/0324504 | A1 | 12/2010 | Chappel et al. |
| 2011/0132480 | A1 | 6/2011 | Chappel |
| 2014/0299544 | A1* | 10/2014 | Wilt ...................... A61M 1/1601 210/646 |

FOREIGN PATENT DOCUMENTS

| | | |
|---|---|---|
| EP | 2253352 A1 | 11/2010 |
| JP | 51-117489 | 10/1976 |
| JP | 09-322936 A | 12/1997 |
| JP | 2004-97703 | 4/2004 |
| JP | 2010-520446 A | 6/2010 |
| WO | 1992/17220 | 10/1992 |
| WO | WO 93/10389 A1 | 5/1993 |
| WO | WO 2009 098314 A1 | 8/2009 |
| WO | WO 2010 020891 A1 | 2/2010 |
| WO | WO 2011 098867 A1 | 8/2011 |
| WO | WO 2011 098946 A1 | 8/2011 |
| WO | WO 2014 108860 A1 | 7/2014 |

OTHER PUBLICATIONS

Written Opinion of the International Searching Authority for PCT/IB2016/054117, dated Nov. 9, 2016.
Japanese Office Action dated Oct. 9, 2020 for application JP2018-500409.
International Preliminary Report on Patentability for PCT/IB2016/054117 dated Jan. 18, 2018.
Japanese Office Action dated Feb. 19, 2020 for application JP2018-500409.

* cited by examiner

SYSTEM AND METHOD FOR CLEANING A FILTER

CROSS REFERENCE TO RELATED APPLICATIONS

The present application is a United States national stage application of International patent application PCT/IB2016/054117 filed on Jul. 8, 2016 designating the United States, and claims foreign priority to European patent application EP 15175963.6 filed on Jul. 8, 2015, the contents of both documents being herewith incorporated by reference in their entirety.

FIELD OF THE INVENTION

The present invention relates to a medical device comprising a filter and elements allowing this filter to be cleaned. The invention also discloses a method used for cleaning the filter.

PRIOR ART

Certain medical devices require the use of a filter so as not to disturb or impair operation thereof. The purpose of this filter is to prevent any particles from reaching an element of the device that might be sensitive thereto. This may for example be a flow restrictor (also referred to as a flow limiter or flow rate limiter) or a valve that could become blocked or damaged by one or more particles which could alternatively impair correct operation thereof. However, the use of such a filter implies that it is probable or even necessary to have to perform regular maintenance on this filter so that the filter itself does not impair the operation of the device (for example when the filter is blocked by numerous particles). In general, this maintenance involves replacing the filter. Unfortunately, when the device is an implanted device, it is often complicated to perform this maintenance and it is necessary to avoid as far as possible the need to extract the device simply in order to clean the filter.

The present document considers the example of a cerebral spinal fluid (CSF) shunt valve device (although the invention is not restricted to this type of device). This type of device is used to treat hydrocephalus and allows excess cerebral spinal fluid to be drained to another part of the body (for example the peritoneum). These devices generally comprise a fluidic path that allows the excess fluid present in the brain to be drained off. The flow rate is regulated through a valve which allows control either of the pressure inside the brain or of the flow rate of liquid passing along the fluidic path. In general, and in this document, this valve can also be referred to as a flow restrictor, a flow regulator, or a shunt valve. This valve may regulate the quantity, direction of flow and pressure of the cerebral spinal fluid leaving the ventricles of the brain. Thus, when the pressure inside the brain increases as a result of an increase in the volume of cerebral spinal fluid, the valve opens and the excess liquid is removed to a cavity situated downstream. The following types of shunt may be used:

- a ventriculo-peritoneal shunt removes liquid from the ventricles of the brain to the abdominal cavity;
- a ventriculo-atrial, or ventriculo-auricular shunt removes fluid from the ventricles of the brain to a chamber of the heart;
- a lumbo-peritoneal shunt removes the liquid from the bottom of the back to the abdominal cavity.

These devices may be positioned behind the ear or near the top of the head.

Unfortunately, the presence of proteins and tissue debris, for example, in this fluid causes these valves and/or the catheters to become obstructed and this obstruction is a significance cause of failure over the course of time. The use of a filter which would hold back these various elements could make it possible to improve the resistance of these valves to obstruction. However, to date, no device of this type contains a filter because the risk of the filter becoming blocked is almost as high as the risk of the device becoming blocked. In addition, because these devices are implanted, it is inconceivable to have to remove the device in order to perform maintenance on such a filter.

GENERAL DESCRIPTION OF THE INVENTION

The present document describes a system and a method making it possible to overcome the problems encountered in the devices of the prior art.

According to a first aspect of the invention, the system is designed to allow easy maintenance of a filter. In cases in which the system is implanted, this aspect of the invention is particularly important because it avoids a device having to be removed in order to be cleaned. In the case of non-implanted devices such as a delivery system, the invention may prove advantageous because it avoids the need to dismantle the system in order to change the filter, thus limiting the handling and contamination of the system.

The device comprises a fluidic path in which are arranged a filter, two cavities (one positioned on each side of the filter) and a flow restrictor. The device is designed to make a fluid flow, in what is referred to as a "normal" mode of operation, along this fluidic path passing in succession through the first cavity, the filter, the second cavity then the flow restrictor. The device is also designed to make a fluid flow, in what is referred to as a "purge" mode of operation, along this same fluidic path passing through the filter, but in the opposite direction to the normal flow of fluid (in the normal mode of operation). Thanks to the "purge" mode, the fluid will detach impurities caught on the filter in order to clean it.

According to a second aspect of the invention, the system disclosed is a cerebral spinal fluid shunt valve that has greater resistance to obstruction. Obstruction may be due to the presence of blood, to a buildup of proteins or more generally to the presence of debris coming from the brain. It has been reported that after 2 years of use of a cerebral spinal fluid shunt valve, the rate of failure caused by occlusion is 20%. Thus, in order to avoid having to explant the device after only 2 years, the invention proposes adding a filtration device (as described hereinabove) to a cerebral spinal fluid shunt valve. For preference, this cerebral spinal fluid shunt valve is placed inside a housing containing a system (filtration device) as disclosed hereinabove so as to be able to clean the filtration device in the least invasive and safest possible way.

According to a third aspect of the invention, the invention relates to a non-invasive (or not very invasive) method of performing maintenance on an implanted filtration device. The method preferably uses the filtration device described in the first aspect of the invention. The method consists in generating a pressure in the cavity so as to force at least some of the pressurized fluid to pass through the filter in the opposite direction to the normal flow mode. In order to do that, a user may squash a volume of fluid for example if the fluid path comprises, at the level of the second cavity, a flexible part, the user may press on this flexible part. Another solution might be to inject a fluid directly into the second cavity using, for example, a syringe or a separate mechanical pump reversibly fluidically connected to the second cavity.

LIST OF FIGURES

The invention will be better understood hereinafter by means of a number of illustrated examples.

It goes without saying that the invention is not restricted to these embodiments.

Figure 1B:
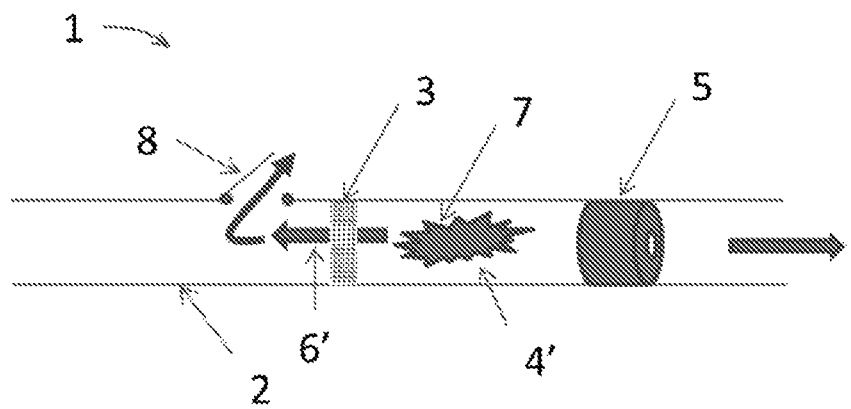

FIGS. 1a and 1b schematically depict the filtration device in two modes of operation.

Figure 2A:
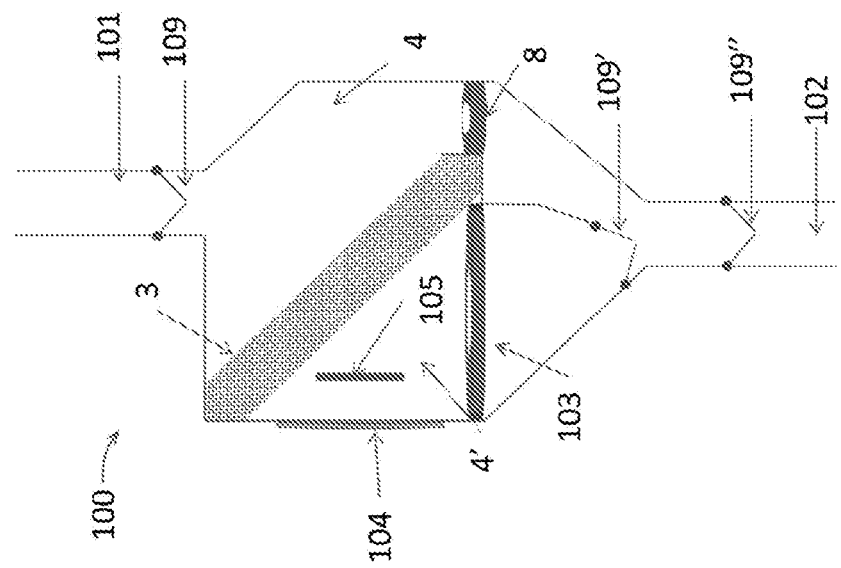
Figure 2B:
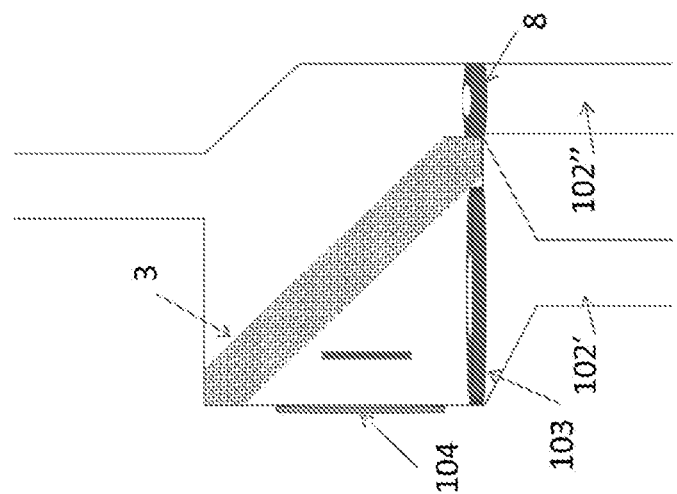

FIGS. 2a and 2b illustrate one embodiment of a shunt system comprising a filtration device.

FIGS. 3a, 3b, 3c and 3d schematically depict three modes of operation of the system.

Figure 4:
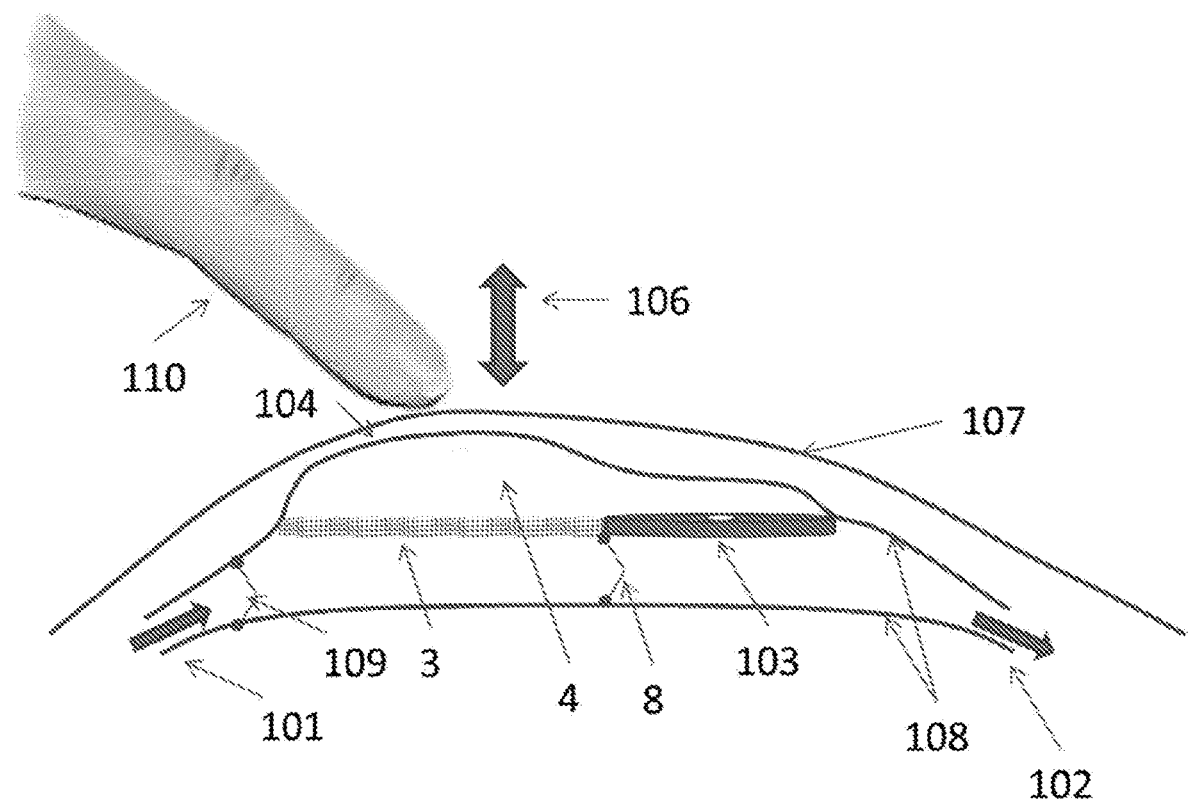

FIG. 4 explains an embodiment implanted under the skin of a patient.

NUMERICAL REFERENCES USED IN THE FIGURES

1 Filtration device
2 Fluidic path
3 Filter
4 First cavity
4' Second cavity
5 Flow restrictor
6 Normal direction of flow
6' Direction of flow in purge mode
7 Pressurization of the fluid in the cavity
8 Purge valve
100 Fluidic shunt system
101 Fluid inlet
102, 102', 102" Fluid outlet
103 Valve
104 Septum or flexible wall
105 Protection
106 Movement of the digit
107 Patient's skin
108 System housing
109 Nonreturn valve
110 Digit

DETAILED DESCRIPTION OF THE INVENTION

In the present document, the detailed description of the invention comprises embodiments of devices, systems and methods which are all given by way of illustration. It should be clearly understood that other embodiments are conceivable and may be added without departing from the scope or spirit of the invention. The detailed description which follows, therefore, should not be interpreted in a restrictive sense.

The present application claims the priority of European application no. EP 15175963.6, filed on Jul. 8, 2015 in the name of Debiotech SA, the entire content of which should be considered to form part of the present application.

Unless indicated otherwise, the scientific and technical terms used in the present document have the meanings commonly used by those skilled in the art. The definitions provided in this document are mentioned to facilitate understanding of the terms frequently used and are not intended to restrict the scope of the invention.

Direction indications used in the description and the claims, such as "top", "bottom", "left", "right", "upper", "lower", and other directions or orientations are mentioned in order to provide more clarity with reference to the figures. These indications are not intended to limit the scope of the invention.

The verbs "to have", "to comprise", "to include" or equivalent are used in the present document in a broad sense and in general mean "includes, without being limited thereto".

The term "or" is generally used in a broad sense encompassing "and/or" unless the context clearly indicates the opposite.

In this document, the terms "upstream" and "downstream" refer to the siting of the elements relative to one another in the normal direction of flow of fluid (namely in the normal mode of operation).

FIGS. 1a and 1b disclose the principle of the two modes of operation of the filtering device (1). This filtering device comprises a fluidic path (2) in which there are arranged, in succession, a first cavity, a filter (3), a second cavity (4) and a flow restrictor (5). According to FIG. 1a, when the mode of operation is what is referred to as the "normal" mode or "normal use" mode, the fluid flows in a direction of flow (6) leading from the filter to the flow restrictor. Whereas when the mode of operation is referred to as the "purge" or "forced" mode, the fluid flows in a direction of flow (6') which leads from the second cavity to the first cavity, passing through the filter, as disclosed in FIG. 1b, and passes through the filter in order to clean it.

The benefit of the flow restrictor (5) may be to force, during a purge, at least part of the fluid to pass through the filter in the opposite direction (6') to the flow in normal mode (normal use). It might be possible to replace the restrictor with (or to add upstream of the flow restrictor but downstream of the second cavity) any other means that limits or prevents the flow of fluid through this means in the second mode of operation. This could be an occlusion means such as a passive or active valve, a flexible chamber or tube that could be crushed or closed by the user in the second mode of operation.

It is possible for a volume fraction of fluid to pass through the flow restrictor nonetheless. In a preferred embodiment, the flow restrictor may be a valve that closes partially or fully when the pressure of the fluid in the cavity reaches a predetermined threshold (for example a flow regulator which regulates the flow over a determined range of pressure of the fluid present in the second cavity). There may also be a fluidic resistance that is constant or variable according to the pressure exerted in the cavity (4).

The device may comprise a purge valve arranged in the region of the first cavity (namely upstream of the filter). In that case, the "purge" mode of operation would make it possible to open the purge valve (8) (as illustrated in FIG. 1b) either thanks to the pressure, because of the direction of flow or through action on the part of the user. For preference, the fluidic path positioned upstream of the first chamber comprises a nonreturn valve or an occlusion means so that the pressurized fluid does not travel back up the fluidic path and so that it is forced to exit via the purge valve. The purge valve (8) can open when the pressure of the fluid near the purge valve reaches a predetermined threshold level or via an actuated mechanism (actuated for example by the digit of a user, medical practioner, patient, etc.) during the purge mode of operation. Particles blocking the filter can thus be removed from the filter and then exit from the main fluidic path via the purge valve. This purge valve may also open when the filter becomes plugged and the pressure upstream of the filter (for example in the first cavity) exceeds a certain threshold whether or not this is because the filter is plugged.

The "purge" mode of operation may be triggered by a means which will pressurize (7) a fluid in the second cavity. This triggering may be the fact of pressing on a flexible zone of the wall of the second cavity or the injection of a fluid into the second cavity using a syringe or a separate mechanical pump reversibly fluidically connected to the second cavity.

The "purge" mode of operation may be triggered after (or when) a differential pressure (pressure differential between the first and second chamber) causes fluid to move from the second cavity towards the first cavity. For example, it is possible to create a raised pressure in the second cavity relative to the pressure in the first cavity. It is also possible to encourage fluid to move by creating a raised pressure in the second cavity and/or reduced pressure in the first cavity. Thus, the flow of the fluid during the second mode of operation is in a direction that is opposite to the flow of fluid in the first mode of operation, at least in the filtering device.

In one embodiment, the filtering device is designed to be implemented in a system comprising a flow regulator such as a cerebral spinal fluid shunt valve. A flow regulator makes it possible either to keep the fluid upstream of the regulator at a determined pressure by varying the flow rate through the regulator (as a preference), or to restrict the flow rate of the regulator despite the variation in pressure upstream of the regulator. Such regulators are described in the international patent applications bearing the following publication numbers: WO 93/10389 A1, WO 2009/098314 A1, WO 2010/020891 A1, WO 2011/098867 A1, WO 2011/098946 A1 and WO 2014/108860 A1. The content of these applications is incorporated by reference into the present document.

This embodiment is illustrated by FIGS. 2a and 2b. These figures set out a fluidic shunt system comprising a fluid inlet (101), at least one fluid outlet (102, 102', 102"), a filter (3), two cavities (4, 4'), a flow regulator (103) and, optionally, a purge valve (8). The filter-cavity-regulator assembly is placed on a first fluidic path and arranged in such a way that, in a first mode of operation, a fluid enters via the fluid inlet (101), passes in succession through the first cavity (4), the filter, the second cavity (4') then the flow regulator and reaches at least one outlet (102, 102'). For preference, the system may comprise a second fluidic path which may comprise a purge valve (8), a flow restrictor or a nonreturn valve. Thus, in order to reach an outlet of the system, the fluid may pass either along the first fluidic path comprising the flow regulator (flow restrictor or valve) or along the second fluidic path (for example the purge valve).

For preference, the filter, the cavity, the flow regulator and the purge valve are arranged inside the one same housing. This housing may be designed to be implanted and may thus be made of a material compatible with this function and/or has a size suited to being implanted in the body of a patient, for example in the nape or ear region.

FIG. 2a shows a device provided with a single fluid outlet into which the fluid coming from the flow regulator (103) and the fluid coming from the purge valve (8) are delivered. FIG. 2b shows a device provided with two separate fluid outlets, one for the fluid coming from the fluid regulator and the other for the fluid coming from the purge valve.

The second cavity (4') is designed so that the fluid contained in this cavity can be pressurized within it.

To this end, one wall of the cavity (which may be one wall of the housing) may comprise:

- a septum (104) so as to allow the tip of a needle to penetrate the cavity and inject a fluid (water, serum, a drug, liquid, gas, etc.). In this case, a protection (105) may be placed in the cavity so as to protect the filter or so as to limit the penetration of the needle. This protection may also make it possible (because of its shape and design) to have better diffusion of the injected fluid so as to unblock the major portion of the filter.
- a flexible wall (104) (for example concave in shape and of sufficient capacity) that a user can crush so as to pressurize the fluid already present in the cavity. A protection (105) may also limit the deformation of the flexible wall.
- any other structure known to those skilled in the art making it possible to increase the pressure in the second cavity (4') (a chemical reaction between two reagents in a sealed pouch that might be positioned inside the second cavity, the two reagents being separated from one another beforehand by a wall which is broken by the user in order to give rise to the piezogenic chemical reaction, etc.).

FIGS. 3a, 3b, 3c and 3d set out 4 possible modes of operation. The mode of operation of FIG. 3a may be called the main mode of operation or first mode of operation or normal mode of operation. A fluid (for example cerebral spinal fluid) enters via the fluid inlet of the shunt system, passes in succession through the first cavity, the filter, the second cavity and the flow regulator in order to reach the fluid outlet. The flow regulator will make it possible to regulate the pressure inside the brain or the flow rate of the fluid in the shunt system.

Figure 3A:
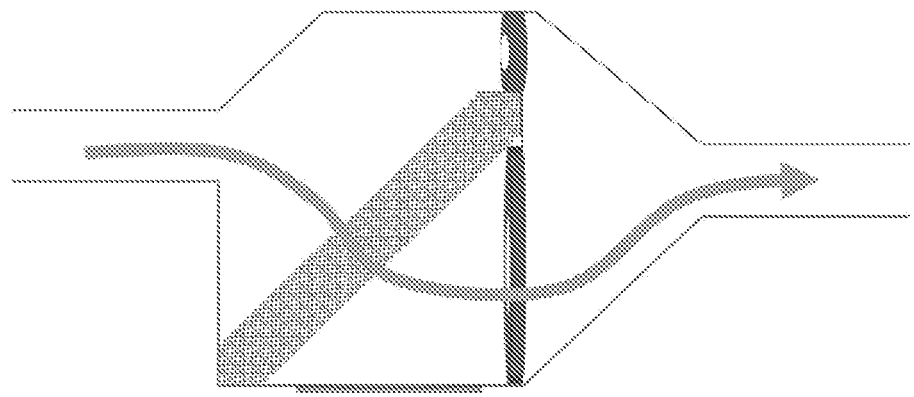
Figure 3B:
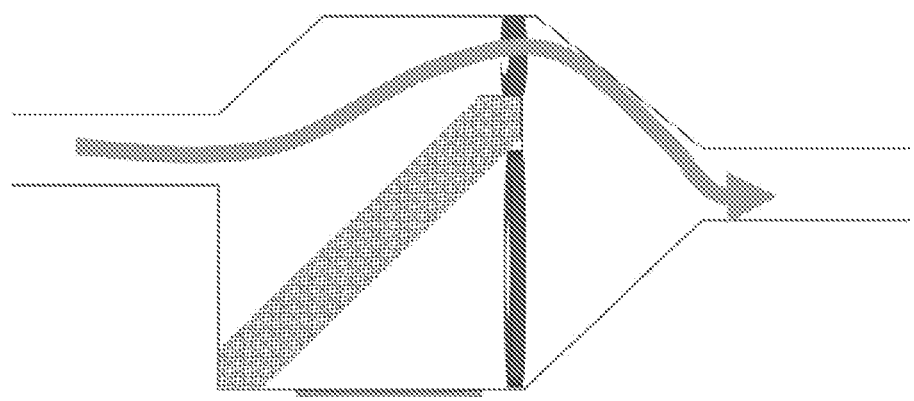

The mode of operation of FIG. 3b makes it possible, in the event of a high pressure in the device, to dump all or some of the fluid through the second fluidic path which may comprise a purge valve or high-pressure valve or nonreturn valve. This valve may be designed to open only when the pressure of the fluid (in the first chamber) reaches a predetermined threshold. This may be a mode of operation that is executed when the filter and/or the flow restrictor is plugged.

Figure 3C:
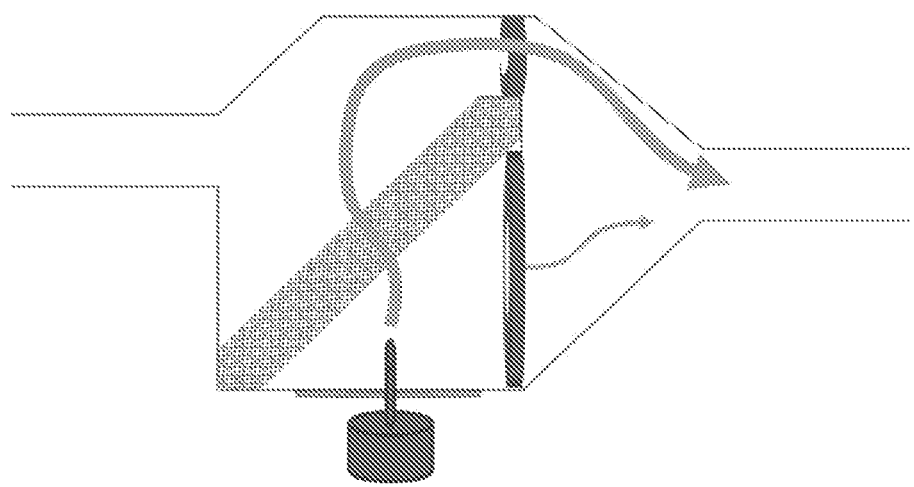
Figure 3D:
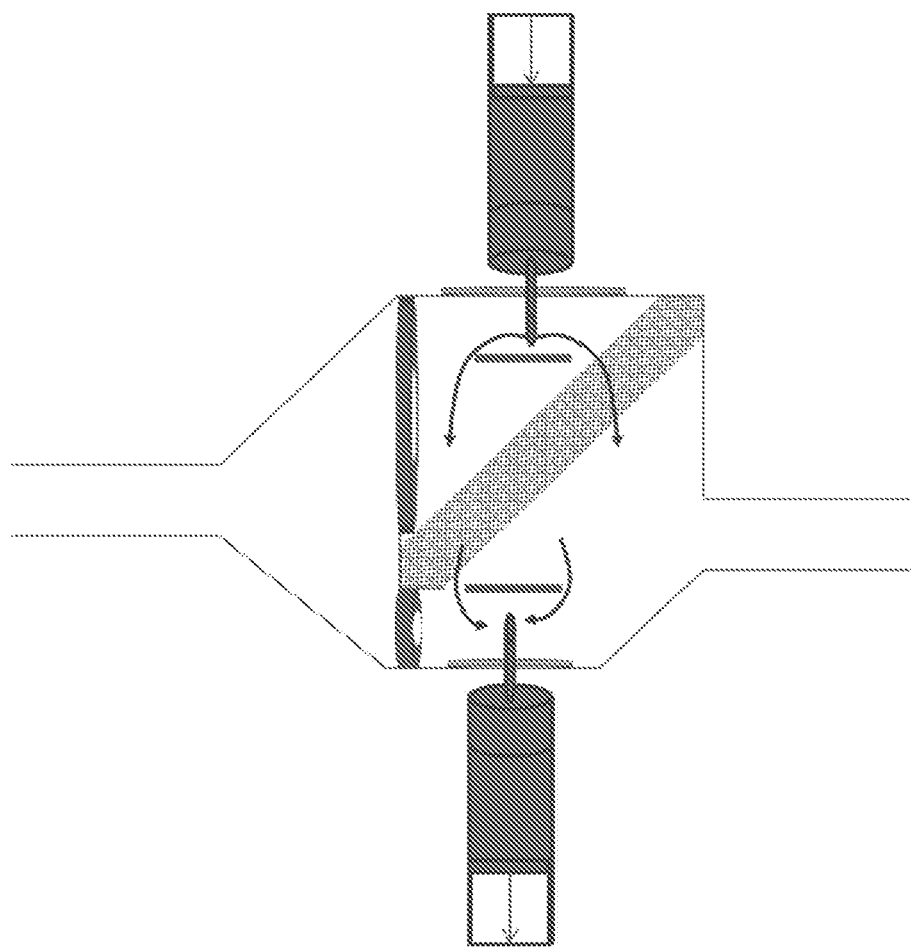

The modes of operation of FIGS. 3c and 3d allow cleaning of the filter. In these examples, a needle pierces the septum of the second cavity so as to inject a fluid into the second cavity. This needle makes reference to a means of fluidic connection of an injection (and, in the case of FIG. 3d, aspiration) device such as a syringe or a more complex device comprising a pump designed to displace a fluid. The pump may be connected to a reservoir designed to contain or receive a fluid (gas or liquid). This fluidic connection means may be connected reversibly to the second cavity or first cavity. In another embodiment, this connection means may be a port connected to a pump and a reservoir all of which forms part of the medical device housed for example in the one same housing.

The injection needs to make it possible to achieve a certain pressure or certain flow rate (higher than the outlet flow rate from the flow regulator). Because not all of the fluid will be able to be discharged by the flow regulator (or if the flow regulator is closed or prevents all or some of the fluid from flowing). Thus, at least some of the injected or pressurized fluid is going to be forced to pass through the filter in the opposite direction to the normal flow (illustrated in FIG. 3a). As disclosed in FIG. 2a, the system may comprise one or more nonreturn valves (109, 109', 109") so as to constrain the flow of the fluid. In particular, the nonreturn valve (109) makes it possible to prevent fluid from exiting via the system fluid inlet, the nonreturn valve (109") makes it possible to prevent fluid from entering via a fluid outlet of the system, and the nonreturn valve (109') makes it possible to avoid the fluid contaminating the flow regulator.

According to one embodiment disclosed in FIG. 3d, the first cavity allows the insertion of a needle so as to aspirate the liquid laden with particles resulting from the cleaning of the filter.

In one embodiment, the second cavity (4) may comprise a membrane dividing said cavity into two distinct and sealed (relative to one another) sub-cavities. The first sub-cavity could be in fluidic communication with the flow regulator and the filter while the second sub-cavity could be in contact with the septum (104). The membrane could be made from a flexible material so that the two sub-cavities are in pressure communication. This embodiment allows a fluid to be injected temporarily into the second cavity using a syringe or a pump (for example). This injection will cause the membrane to move and this will have the effect of increasing the pressure in the other sub-cavity so as to clean the filter. The fluid added may then be partially or fully removed from the second sub-cavity. This construction involving two sub-cavities makes it possible to avoid any microbial contamination during purge and/or to avoid introducing air into the device. In another embodiment, the system could not comprise the septum and the intermediate membrane could be moved by some other means known to those skilled in the art, for example by an actuator (electronic or otherwise) such as a piezoelectric actuator.

According to one embodiment disclosed through FIG. 4, a shunt system is implanted under the skin (107) of a patient. The fluid inlet (101) and the fluid outlet (102) may be connected to catheters which have not been depicted in FIG. 4. The system is protected inside a housing (108) which comprises a flexible part (104). The digit (105) of a user may press (106) on the flexible part (104) so as to increase the pressure in the cavity and force the fluid to pass along the second fluidic path comprising the purge valve (8) (which may also have the function of a nonreturn valve). The user may effect several movements (106) of the digit in order to prime a pumping mechanism that allows the filter to be cleaned or that makes it possible to force shunting. For example, in the event of a high pressure within the brain the patient may suffer severe headaches and the act of pumping will allow him quickly to relieve his headaches and clean the filter.

The filter ideally has a large filtration area, with a pore size suited to the dimensions of the flow regulator. The pore size may vary between 0.1 µm and 10 µm, with a typical size of 1 µm. The material of the filter may be hydrophilic in order to limit the adsorption of proteins. The pore density may be comprised between 0.1% and 30%. The thickness of the filter may be comprised between 0.01 mm and 10 mm. The filtration area may be comprised between 0.1 cm$^2$ and 100 cm$^2$.

A mechanical support may be needed (support mesh, etc.) to hold the filter appropriately in the system during purging, because a pressure of several bar may be generated by a syringe or a pump.

The system may comprise a prefilter with a pore size>1 µm. This prefilter may be oriented at right angles to the direction of the flow during a high raised pressure which causes the purge valve to open, so as to direct the largest debris towards the outlet.

The system may further contain a pressure sensor which can be read and powered by wireless technology (induction, microwave, radio, etc.). This sensor may notably allow diagnostics to be performed on the system and, in the event of the suspicion of occlusion, a purge may be effected before the patient starts to feel the first symptoms.

For preference, the flow regulator is adjustable, which means to say that it can be adjusted after reading of the pressure sensor so as to partially open or close it during purge or after detection of an occlusion. If the purge proves ineffectual, an adjustment of the opening of the valve may be needed in order to prevent a surgical intervention. Likewise, the purge valve may be adjustable and thus make it possible to adjust the system to suit the physiology and characteristics of the patient (the height of water column, which means to say the difference in height between the top of the device (the brain) and the other end via which the fluid reemerges from the system (for example the peritoneal cavity, etc.).

The pressure sensor may be an absolute-pressure sensor positioned upstream of the filter so as to determine with precision the pressure within the brain. In this way, the sensor could make it possible to perform diagnosis both on the device and on the therapy. A flow meter positioned near the fluid inlet or near the fluid outlet could also make it possible to diagnose the device and the patient. The flow meter may be a thermal flow meter comprising a resistive heating element and two temperature sensors positioned one upstream and one downstream of the heat source.

As disclosed in FIG. 2b, the system may comprise two separate fluid outlets (two catheters or a double-lumen catheter), each of these outlets being able to be connected respectively to the flow regulator and to the purge valve. That makes it possible to limit the occlusion of the catheter or of the lumen on the outlet side of the flow regulator and prevent any contamination of the outlet of the flow regulator (as explained hereinabove).

According to one embodiment, the flow regulator and the purge valve may be two distinct devices connected in parallel (e.g. using tubes).

In one embodiment, the filtering device is connected to a vibrating device (for example of piezoelectric type), which makes it possible to apply vibrations to the system and to detach debris from said filter. This vibrator could be powered by a wired or wireless system (induction, microwave, radio, etc.).

According to one preferred embodiment, a medical device comprises a fluid intake orifice, a fluid outlet orifice, a first cavity, a second cavity, a means for increasing the pressure in the second cavity, a filtering device and a flow restrictor all of which are arranged in such a way that, in a first mode of operation, a fluid enters via the fluid inlet orifice and passes in succession through the first cavity, the filtering device, the second cavity and the flow restrictor in order to reach the fluid outlet orifice. The second cavity is designed to allow an increase in the pressure within it by virtue of said means (to increase the pressure in the second cavity) so that, in a second mode of operation, the compressed fluid (compressed by virtue of said means) passes from the second cavity to the first cavity by passing through the filtering device. In other words, the means for increasing the pressure in the second cavity is designed to allow the medical device to operate in a second mode of operation. All of the features disclosed in this document are compatible with this embodiment.

For preference, the fluid inlet orifice of the medical device comprises a nonreturn valve so that during the second mode of operation, the compressed fluid does not exit via the fluid inlet orifice.

The means for increasing the pressure in the second cavity may comprise a fluid inlet orifice through which a fluid can be injected directly into the second cavity without passing through the fluid inlet orifice. In addition, the means for increasing the pressure in the second cavity may also comprise a septum designed for the insertion of a needle and optionally a protection element positioned facing the septum in the cavity so that a needle cannot damage an element of the medical device such as the filtering device.

The flow restrictor may be a valve, a nonreturn valve, an antisiphon valve, a flow regulator with fixed or variable fluidic resistance or an occlusion means.

The medical device may comprise a second fluid outlet orifice able to allow allows flow to the outside of the medical device in the second mode of operation. Furthermore, the second fluid outlet orifice may comprise a valve which may be a nonreturn valve.

The first cavity may be designed so that a needle can be inserted for withdrawing all or some of the fluid during the second mode of operation.

The means for increasing the pressure in the second cavity may comprise a flexible wall designed to be compressed by a user or another fluid so as to pressurize the fluid present in the second cavity.

The medical device may comprise a pressure sensor. The pressure sensor may be an absolute-pressure sensor. The pressure sensor may be positioned upstream of the filtering device in the direction of flow of fluid of the first mode of operation. The pressure sensor may be positioned downstream of the filtering device but upstream of the fluid restrictor in the direction of flow of fluid of the first mode of operation.

The pore size of the filtering device may vary between 0.1 µm and 10 µm, preferably 1 µm. The thickness of the filtering device may be comprised between 0.01 mm and 10 mm. The filtering area may be comprised between 0.1 cm$^2$ and 100 cm$^2$. The material of the filtering device or the coating of the filtering device may be hydrophobic so as to limit the adsorption of proteins by the filtering device. The pore density of the filter may be comprised between 0.1 and 30%.

According to an alternative embodiment, the medical device is able not to comprise a flow restrictor, and in this case the core of the invention relates to a means of cleaning the filter positioned upstream of a device that is to be protected. In this case, the medical device may comprise an occlusion means positioned downstream of the second cavity. In this case, the medical device may comprise a fluid inlet orifice, a fluid outlet orifice, a first cavity, a second cavity, a means for increasing the pressure in the second cavity, a filtering device, and a (partial or total) occlusion means all positioned in such a way that, in a first mode of operation, a fluid enters via the fluid inlet orifice and passes in succession through the first cavity, the filtering device, the second cavity and the occlusion means in order to reach the fluid outlet orifice. The second cavity is designed to allow an increase in the pressure within it by virtue of said means (for increasing the pressure in the second cavity) so that in a second mode of operation the fluid passes from the second cavity to the first cavity by passing through the filtering device. It being possible for the occlusion means to be activated by the user in order to avoid or limit the flow of fluid through the occlusion means during the second mode of operation. All of the features disclosed in this document are compatible with this embodiment. It would also be possible to have a flow restrictor downstream of the occlusion means.

The invention also relates to a method for cleaning a filter of a medical device as disclosed hereinabove for example comprising a means of access allowing a fluid (stored in an external reservoir, for example a syringe) to be injected into the second cavity (which may or may not comprise a membrane dividing it into two sub-cavities), it being possible for said method to comprise the following steps:
  placing the reservoir and the second cavity into fluidic communication with one another for example by inserting a needle through the means of access to the second cavity (for example a septum),
  injecting the fluid (previously present in the reservoir) into the second cavity at a flow rate and/or at a pressure that is determined so as to make it possible to reverse the direction of flow (for example at a pressure higher than the threshold pressure at which the purge valve opens) (for example for a determined duration or for a determined injected volume),
  optionally removing fluid coming from the first cavity (if the device comprising a means of access to the first cavity via a needle for example) or from the second cavity (for example if the second cavity comprises a membrane dividing it into two sub-cavities),
  fluidically disconnecting the reservoir from the second cavity, for example by withdrawing the needle,
  optionally repeating the operation.

The invention also describes another method for cleaning a filter of a medical device as disclosed hereinabove for example comprising a flexible wall (for example of concave shape so as to create a reservoir of fluid in the second cavity that is sufficient in size to cause the displacement of a volume needed for cleaning) on which the user may apply pressure in order to raise the pressure in the second cavity, said method may comprise the following steps:
  pressing the flexible part of the system,
  releasing the pressure,
  optionally repeating that operation.
Other steps may be added to one of these two methods:
  measuring the pressure, or
  measuring the flow rate, or
  performing adjustment according to the measurements from the flow regulator, or
  performing adjustment according to the measurements from the purge valve, or
  activating or closing one or more occlusion means, or
  inserting a needle into the first cavity in order to aspirate particle-laden fluid.

The invention claimed is:

1. A medical device for controlling a fluid flow comprising:
  a fluid inlet orifice;
  a fluid outlet orifice;
  a first cavity;
  a second cavity including a flexible wall configured to be deformed to increase a pressure in the second cavity;
  a filter fluidically arranged between the first and the second cavity; and
  a flow restrictor,
  wherein the medical device is configured to operate in a first mode in which a fluid enters via the fluid inlet orifice and passes in succession through the first cavity, the filter in a first direction, the second cavity, and the flow restrictor to reach the fluid outlet orifice, and
  wherein the medical device is configured to operate in a second mode in which the flexible wall is deformed to pass at least a portion of the fluid present in the second cavity through the filter in an opposite direction to the first direction.

2. The medical device as claimed in claim 1, wherein the second cavity includes a fluid intake orifice through which a fluid can be injected directly into the second cavity without entering through the fluid inlet orifice.

3. The medical device as claimed in claim 2, wherein the second cavity further includes a septum configured to insert a needle.

4. The medical device as claimed in claim 3, wherein the second cavity further includes a protection element positioned to face the septum in the cavity to prevent the needle from damaging an element of the medical device.

5. The medical device as claimed in claim 1, wherein the flow restrictor includes at least one of a valve, a non-return valve, an anti-siphon valve, a flow regulator with fixed fluidic resistance, a flow restrictor with variable fluidic resistance, and an occlusion device.

6. The medical device as claimed in claim 1, further comprising:
a second fluid outlet orifice configured to permit a flow of the fluid to an outside area of the medical device in the second mode.

7. The medical device as claimed in claim 6, wherein the second fluid outlet orifice comprises a valve.

8. The medical device as claimed in claim 7, wherein the valve of the second fluid outlet orifice includes a non-return valve.

9. The medical device as claimed in claim 7, wherein the first cavity is configured such that a needle can be inserted to withdraw all or some of the fluid during the second mode.

10. The medical device as claimed in claim 1 further comprising:
a pressure sensor.

11. The medical device as claimed in claim 10, wherein the pressure sensor includes an absolute pressure sensor.

12. The medical device as claimed in claim 11, wherein the pressure sensor is positioned upstream of the filtering device when referenced to the first direction of the fluid flow.

13. The medical device as claimed in claim 1, wherein a pore size of the filter is between 0.1 µm and 10 µm.

14. The medical device as claimed in claim 1, wherein a pore size of the filter is about 1 µm.

15. The medical device as claimed in claim 1, wherein a thickness of the filter is between 0.01 mm and 10 mm.

16. The medical device as claimed in claim 1, wherein a filtration area of the filter is between 0.1 $cm^2$ and 100 $cm^2$.

17. The medical device as claimed in claim 1, wherein at least one of a material of the filter and a coating of the filter is hydrophobic to limit adsorption of proteins by the filter.

18. The medical device as claimed in claim 1, wherein a pore density of the filter is between 0.1% and 30%.

19. A medical fluid flow device comprising:
a first chamber;
a second chamber including a flow regulator for fluid flowing out from the second chamber, and a flexible wall; and
a filter fluidically arranged between the first chamber and the second chamber configured to remove particles from a fluid flowing from the first chamber to the second chamber,
wherein the flexible wall is configured to be deformed to increase a fluid pressure in the second chamber so that a portion of the pressurized fluid can flow in a reverse direction through the filter from the second chamber to the first chamber and thereby removes particles from the filter.

* * * * *